US00PP19314P2

(12) United States Plant Patent
Spruit

(10) Patent No.: US PP19,314 P2
(45) Date of Patent: Oct. 14, 2008

(54) ***ZAMIOCULCAS* PLANT AND NAMED "ZAMICRO"**

(50) Latin Name: *Zamioculcas zamiifolia*
Varietal Denomination: Zamicro

(75) Inventor: Adrianus Theodorus Spruit, Aarlanderveen (NL)

(73) Assignee: Aardam Planten B.V., Aarlanderveen (NL)

( * ) Notice: Subject to any disclaimer, the term of this patent is extended or adjusted under 35 U.S.C. 154(b) by 0 days.

(21) Appl. No.: 11/974,213

(22) Filed: Oct. 11, 2007

(51) Int. Cl.
*A01H 5/00* (2006.01)

(52) U.S. Cl. ..... Plt./263.1
(58) Field of Classification Search ..... Plt./263.1
See application file for complete search history.

(56) References Cited

PUBLICATIONS

UPOV–ROM for PBR 20040736 for cultivar Zamicro, 1 page.*

* cited by examiner

*Primary Examiner*—Annette H Para
(74) *Attorney, Agent, or Firm*—C. A. Whealy

(57) ABSTRACT

A new and distinct cultivar of *Zamioculcas* plant named 'Zamicro', characterized by its upright and compact growth habit; relatively small leaves; and shiny dark green-colored leaves.

2 Drawing Sheets

Botanical designation: *Zamioculcas zamiifolia.*
Cultivar denomination: 'Zamicro'.

BACKGROUND OF THE INVENTION

The present invention relates to a new and distinct cultivar of *Zamioculcas,* botanically known as *Zamioculcas zamiifolia,* and hereinafter referred to by the name 'Zamicro'.

The new *Zamioculcas* is a naturally-occurring whole plant mutation of an unidentified selection of *Zamioculcas zamiifolia.* The new *Zamioculcas* was discovered and selected by the Inventor as a single plant from within a population of plants of the parent selection in a controlled environment in Aarlanderveen, The Netherlands in 2002.

Asexual reproduction of the new *Zamioculcas* by vegetative cuttings in a controlled environment in Aarlanderveen, The Netherlands, has shown that the unique features of this new *Zamioculcas* are stable and reproduced true to type in successive generations.

SUMMARY OF THE INVENTION

The cultivar Zamicro has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Zamicro'. These characteristics in combination distinguish 'Zamicro' as a new and distinct cultivar of *Zamioculcas:*

1. Upright and compact growth habit.
2. Relatively small leaves.
3. Shiny dark green-colored leaves.

Plants of the new *Zamioculcas* can be compared to plants of the parent selection. Plants of the new *Zamioculcas* differ from plants of the parent selection in the following characteristics:

1. Plants of the new *Zamioculcas* are more compact and shorter than plants of the parent selection.
2. Plants of the new *Zamioculcas* have smaller leaves than plants of the parent selection.

Plants of the new *Zamioculcas* can be compared to plants of the *Zamioculcas zamiifolia* cultivar ZZ, not patented. In side-by-side comparisons conducted in Aarlanderveen, The Netherlands, plants of the new *Zamioculcas* differed from plants of the cultivar ZZ in the following characteristics:

1. Plants of the new *Zamioculcas* were more compact and shorter than plants of the cultivar ZZ.
2. Plants of the new *Zamioculcas* had smaller leaves than plants of the cultivar ZZ.

BRIEF DESCRIPTION OF THE PHOTOGRAPHS

The accompanying colored photographs illustrate the overall appearance of the new *Zamioculcas* showing the colors as true as it is reasonably possible to obtain in colored reproductions of this type. Colors in the photographs may differ slightly from the color values cited in the detailed botanical description which accurately describe the colors of the new *Zamioculcas.*

The photograph on the first sheet comprises a side perspective view of a typical plant of 'Zamicro' grown in a container.

The photograph on the second sheet is a close-up view of a typical branch of 'Zamicro'.

DETAILED BOTANICAL DESCRIPTION

The aforementioned photographs and following observations, measurements and values describe plants of the new *Zamioculcas* grown in Aarlanderveen, The Netherlands in a glass-covered greenhouse during the winter and spring and under conditions which closely approximate commercial production. During the production of the plants, day temperatures ranged from 20° C. to 30° C., night temperatures ranged from 18° C. to 22° C. and light levels averaging 100 kilolux. Plants had been growing in 8.5-cm containers for about seven months when the photographs and the description were taken. In the detailed description, color references are made to The Royal Horticultural Society Colour Chart, 2001 Edition, except where general terms of ordinary dictionary significance are used.

Botanical classification: *Zamioculcas zamiifolia* cultivar Zamicro.

Parentage: Naturally-occurring whole plant mutation of an unidentified selection of *Zamioculcas zamiifolia.*

Propagation:

*Type.*—By vegetative cuttings.

*Time to initiate roots, summer.*—About three weeks at temperatures of 20° C. to 30° C.

*Time to initiate roots, winter.*—About one month at temperatures of 20° C. to 25° C.

*Time to produce a rooted young plant, summer.*—About 20 weeks at temperatures of 22° C. to 30° C.

*Time to produce a rooted young plant, winter.*—About 29 weeks at temperatures of 20° C. to 25° C.

*Root description.*—Medium in thickness to thick, fleshy; white to light brown in color.

*Rooting habit.*—Freely branching; dense.

Plant description:

*Plant habit.*—Upright and compact growth habit; narrow inverted triangle. Stemless; pinnately compound leaves developing in basal rosettes; typically about three basal rosettes develop per plant. Appropriate for 8.5-cm and larger containers. Low vigor.

*Plant height.*—About 23 cm.

*Plant diameter.*—About 20 cm.

Foliage description:

*Arrangement.*—Pinnately compound; about three to four leaves per basal rosette each with about ten leaflets; leaflets sessile.

*Leaves.*—Length: About 20.4 cm. Width: About 7 cm. Petiole diameter, base: About 9 mm. Petiole diameter, at the lowermost leaflet: About 4 mm. Petiole texture: Smooth, glabrous. Petiole color: Close to 148A.

*Leaflets.*—Length: About 4.6 cm. Width: About 1.7 cm. Thickness: About 0.6 mm. Shape: Elliptic; slightly concave. Apex: Acute. Base: Attenuate. Margin: Entire. Texture, upper and lower surfaces: Glabrous, smooth; thick, glossy. Venation pattern: Pinnate. Color: Developing leaflets, upper surface: Close to 143A. Developing leaflets, lower surface: Between 143B and 144A. Fully expanded leaflets, upper surface: Between 137A and 147A; venation, close to 146B. Fully expanded leaflets, lower surface: Close to 137B; venation, 146B.

Flower description: Flower development has not been observed.

Temperature tolerance: Plants of the new *Zamioculcas* have been observed to tolerate temperatures from about 18° C. to about 32° C.

Pathogen/pest resistance: Plants of the new *Zamioculcas* have not been observed to be resistant to pests and pathogens common to *Zamioculcas.*

It is claimed:

1. A new and distinct *Zamioculcas* plant named 'Zamicro' as illustrated and described.

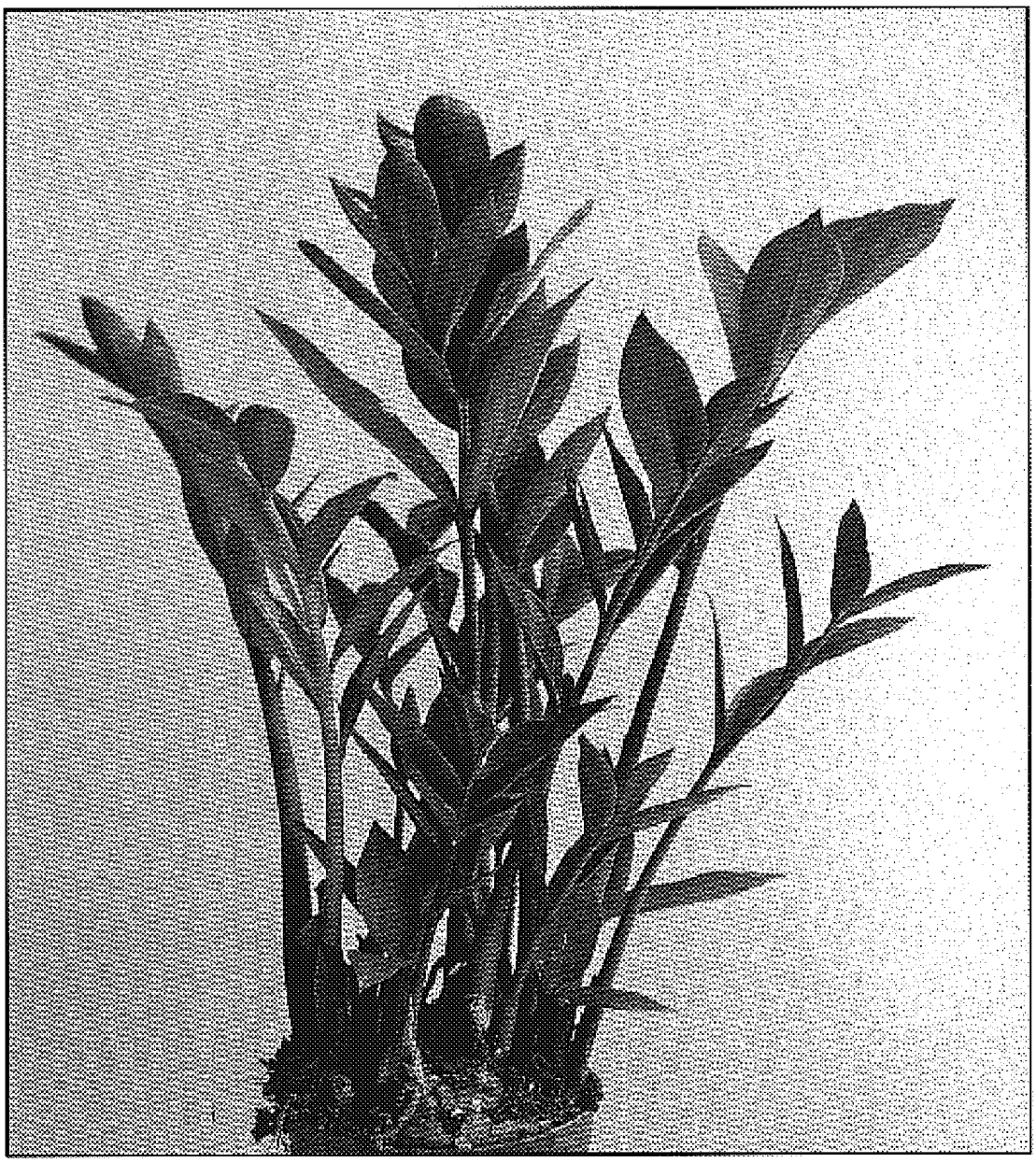

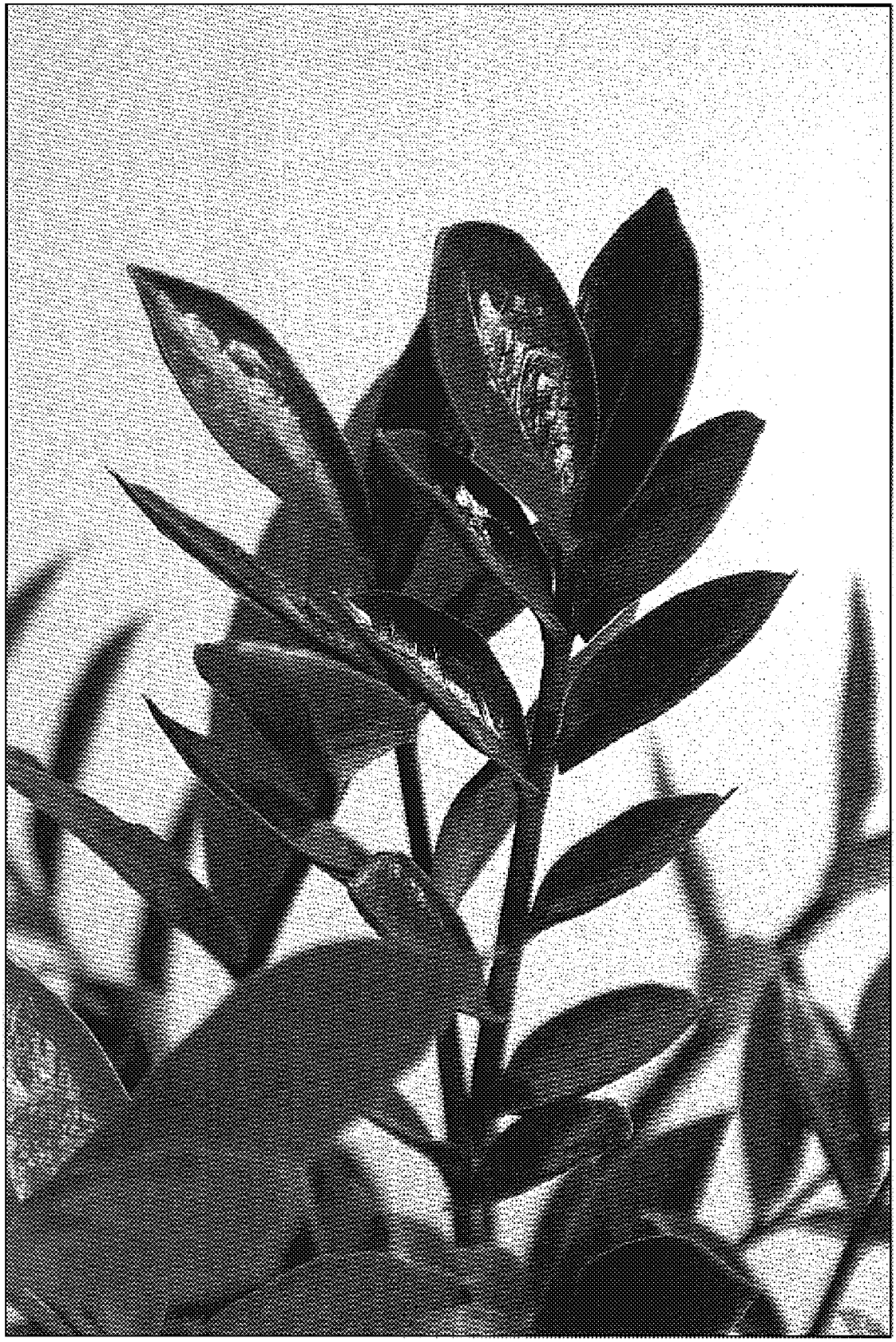

* * * * *